United States Patent
Andrews et al.

[11] Patent Number: 5,761,743
[45] Date of Patent: Jun. 9, 1998

[54] FINGER COT AND METHOD OF MANUFACTURING FINGER COT

[75] Inventors: Warren L. Andrews, Chicago, Ill.; Paula Gordon, The Woodland, Tex.

[73] Assignee: Marmon Holdings, Inc., Chicago, Ill.

[21] Appl. No.: 673,652

[22] Filed: Jun. 28, 1996

[51] Int. Cl.⁶ .......................... A41D 19/00; A41D 27/00
[52] U.S. Cl. .......................... 2/21; 2/167; 2/169; 2/163; 2/161.7
[58] Field of Search ........................ 2/21, 158, 159, 2/160, 161.1, 161.2, 161.3, 161.4, 161.5, 161.6, 161.7, 161.8, 163, 164, 165, 166, 167, 168, 169; 15/227

[56] References Cited

U.S. PATENT DOCUMENTS

| | | |
|---|---|---|
| 911,838 | 2/1909 | Napier . |
| 1,010,283 | 11/1911 | Loy . |
| 1,066,480 | 7/1913 | Finlay . |
| 1,144,777 | 6/1915 | Over . |
| 1,362,461 | 12/1920 | Anast . |
| 1,612,822 | 1/1927 | Jones . |
| 1,664,542 | 4/1928 | Douglass . |
| 1,755,014 | 4/1930 | Morrison . |
| 1,916,921 | 7/1933 | Dougan . |
| 2,039,505 | 5/1936 | Vollmer ........................ 2/20 |
| 2,083,935 | 6/1937 | Arnold ....................... 2/161.6 |
| 2,335,320 | 11/1943 | Swietek ........................ 2/163 |
| 2,434,315 | 1/1948 | Gross ............................ 2/21 |
| 2,461,872 | 2/1949 | Beatty ........................... 2/21 |
| 2,522,842 | 9/1950 | Scholl ............................ 2/21 |
| 2,722,706 | 11/1955 | Chopp ........................ 15/227 |
| 2,725,570 | 12/1955 | Penna .......................... 2/163 |
| 2,847,005 | 8/1958 | Bourne ....................... 128/157 |
| 3,039,460 | 6/1962 | Chandler ..................... 128/87 |
| 3,132,648 | 5/1964 | Scholl ........................ 128/153 |
| 3,147,486 | 9/1964 | Dreyling ......................... 2/1 |
| 3,164,841 | 1/1965 | Burtoff ......................... 2/161 |
| 3,263,681 | 8/1966 | Nechtow et al. ............ 128/157 |
| 3,263,682 | 8/1966 | Rosenfield ................. 128/157 |
| 3,306,288 | 2/1967 | Rosenfield ................. 128/157 |
| 3,382,138 | 5/1968 | Barth .......................... 161/190 |
| 3,511,242 | 5/1970 | Agnone ...................... 128/303 |
| 3,526,224 | 9/1970 | Potts .......................... 128/156 |
| 3,593,803 | 7/1971 | Ibach ......................... 172/370 |
| 3,633,216 | 1/1972 | Schonholtz .................. 2/168 |
| 3,675,264 | 7/1972 | Storandt ...................... 15/227 |
| 3,975,929 | 8/1976 | Fregeolle ................... 66/172 E |
| 3,983,870 | 10/1976 | Herbert et al. ............ 128/165 |
| 4,084,584 | 4/1978 | Detty ......................... 128/80 |
| 4,127,222 | 11/1978 | Adams ....................... 223/101 |
| 4,272,849 | 6/1981 | Thurston et al. ............. 2/16 |
| 4,497,072 | 2/1985 | Watanabe .................. 2/161 A |
| 4,507,807 | 4/1985 | Karkanen .................. 2/161 R |
| 4,514,460 | 4/1985 | Johnson ..................... 428/245 |
| 4,534,354 | 8/1985 | Bonner, Jr. et al. ........ 128/402 |
| 4,660,228 | 4/1987 | Ogawa et al. ............... 2/167 |
| 4,681,012 | 7/1987 | Stelma et al. ............... 84/422 |
| 4,733,410 | 3/1988 | Glotkin ......................... 2/21 |
| 4,742,578 | 5/1988 | Seid ............................. 2/2.5 |
| 4,751,747 | 6/1988 | Banks et al. .................. 2/21 |
| 4,753,231 | 6/1988 | Lang et al. ................ 128/156 |
| 4,774,727 | 10/1988 | Jackson ..................... 2/161 R |
| 4,779,290 | 10/1988 | Welch ........................ 2/161 R |

(List continued on next page.)

FOREIGN PATENT DOCUMENTS

WO9102466   3/1991   WIPO .................... A41D 19/00

*Primary Examiner*—Jeanette E. Chapman
*Attorney, Agent, or Firm*—Rudnick & Wolfe

[57] ABSTRACT

A finger cot intended for surgical use, and a method for manufacturing the finger cot. The finger cot is formed from two blanks, a first blank forms the back portion, and a second forms the palm face, sides and tip. The blanks are formed of materials to provide the desired degree of protection from cuts and punctures, balanced against the degree of sensitivity or tactility needed to perform a specific task. The second blank is place on a anvil having a cavity therein shaped like a finger. An insert is placed over the second blank and forced into the cavity to shape the second blank. A seam, surrounding the cavity, and located on the outside of the finger cot is formed by ultra sonic welding.

5 Claims, 3 Drawing Sheets

U.S. PATENT DOCUMENTS

| | | | |
|---|---|---|---|
| 4,858,245 | 8/1989 | Sullivan et al. | 2/21 |
| 4,864,661 | 9/1989 | Gimbel | 2/167 |
| 4,873,998 | 10/1989 | Joyner | 128/879 |
| 4,877,661 | 10/1989 | House et al. | 428/34.9 |
| 4,888,829 | 12/1989 | Kleinerman et al. | 2/167 |
| 4,901,372 | 2/1990 | Pierce | 2/167 |
| 4,926,851 | 5/1990 | Bulley | 128/157 |
| 4,942,626 | 7/1990 | Stern et al. | 2/161 R |
| 4,964,174 | 10/1990 | Martin | 2/161 R |
| 4,995,119 | 2/1991 | Coolkind | 2/163 |
| 5,036,551 | 8/1991 | Dailey et al. | 2/167 |
| 5,070,540 | 12/1991 | Bettcher et al. | 2/2.5 |
| 5,070,543 | 12/1991 | Beck | 2/163 |
| 5,087,499 | 2/1992 | Sullivan | 428/85 |
| 5,088,125 | 2/1992 | Ansell et al. | 2/167 |
| 5,113,532 | 5/1992 | Sutton | 2/167 |
| 5,146,628 | 9/1992 | Herrmann et al. | 2/161 R |
| 5,154,690 | 10/1992 | Shiono | 602/5 |
| 5,165,114 | 11/1992 | Dams et al. | 2/168 |
| 5,224,363 | 7/1993 | Sutton | 66/202 |
| 5,231,700 | 8/1993 | Cutshall et al. | 2/161 |
| 5,259,069 | 11/1993 | Gimbel | 2/163 |
| 5,261,393 | 11/1993 | Weinzweig | 128/26 |
| 5,263,923 | 11/1993 | Fujimoto | 602/62 |
| 5,267,945 | 12/1993 | Doctor et al. | 602/14 |
| 5,345,612 | 9/1994 | Stein | 2/168 |
| 5,352,216 | 10/1994 | Shiono et al. | 604/312 |
| 5,362,306 | 11/1994 | McCarver et al. | 602/60 |

FINGER COT AND METHOD OF MANUFACTURING FINGER COT

BACKGROUND OF THE INVENTION

I. Field of the Invention

This invention relates to providing a finger cot intended for use in the medical field for protecting the distal end of a wearer's finger from puncture and cut wounds. More particularly, it relates to providing a finger cot which may be placed over a finger tip, over or under a latex glove if desirable, with relative ease and be self retained thereon. It further relates to a method of assembling the finger cot from fabric type material.

II. Description of Related Art Including Information Disclosed Under 37 C.F.R. §§ 1.97 and 1.98

Finger cots and gloves with various types of reinforced finger tips have been provided in the past for better enabling the user to perform particular types of task or to protect a users fingers from injury. More particularly, finger cots and gloves have been provided to protect surgeons and surgical assistants from cutting and puncture wounds which might be inflicted by sharp medical instruments such as scalpels and needles. Examples of the finger cots and gloves are represented by the following U.S. Pat. Nos.:

| U.S. Pat. No. | Inventor | Issue Date |
| --- | --- | --- |
| 3,511,242 | Agnone | 05/12/70 |
| 4,733,410 | Glotkin | 03/29/88 |
| 4,858,245 | Sullivan et al | 08/22/89 |
| 4,864,661 | Gimbel | 09/12/89 |
| 4,873,998 | Joyner | 10/17/89 |
| 4,901,372 | Pierce | 02/20/90 |
| 4,942,626 | Stern et al | 07/24/90 |
| 5,070,543 | Beck | 12/10/91 |
| 5,259,069 | Gimbel | 11/09/93 |

The Agnone, Glotkin, and Sullivan et al patents disclose finger cots, with those set forth in the Agnone and Sullivan et al patents intended to provide protection in surgical uses. The Joyner patent set forth a surgical hand protector system including a hardened molded material covering the palm and lower knuckles, and thimbles of the same material to cover the finger tips, which may be worn under surgical latex gloves. The remaining patents disclose surgical gloves, in the Beck patent gloves and finger cots, which are provided with selected cut and puncture resistant areas.

SUMMARY OF THE INVENTION

It is an object of this invention to provide a finger cot which is particular useful for providing protection from puncture and cut wounds to a finger of a medical worker. It is another object of the invention to provide a method of manufacturing a finger cot which results in a finger cot shaped to be readily received on the finger of a user. It is a further object of the invention to manufacture the finger cot from materials which may not only be shaped in the manufacturing process to receive a finger, but which also provide both cut and puncture resistance and which are elastic so as to stretch over the finger and retain the cot thereon. It is a further object of this invention to form the finger cot from pieces of fabric which are joined together in seams which are located toward the backside of the finger, away from the palm side of the finger, so as not to interfere with the tactile feel of the palm face and tip of the user's finger. It is a still further object of this invention to provide a finger cot which may be provided with a relatively stiff reinforcing member on the palm face, sides and tip of the finger to distribute the force of pushing on an object with a small surface area, such as a needle or the back edge of a knife over a larger portion of the finger surface.

In accordance with this invention, a finger cot is provided which is readily manufactured using a variety of materials. In the preferred embodiment a finger cot is formed from two pieces of material, comprising one or more layers, which may be welded to itself to form a seam. Two or more layers of material are provided toward the tip end of the cot to increase puncture resistance, while only a single layer of material is provided for the remainder of the cot closer to the palm, which provides great stretch and comfort for the user. Alternatively, two layers of material may also be used for the body of the cot to provide added puncture resistance to that area. The material may be a composite of two layers, one of which can be bonded to the other, and also to itself. A first piece of the material is placed over a surface having an indentation therein conforming to the shape of the palm side of a finger. The first piece of material is depressed into the indentation and a second piece of the material is then placed over the first piece, thus molding a cot which conforms to the shape of a finger. An energy source is then applied around the edges of the indentation to bond the first and second pieces of material to each other so as to form a seam which is located outside of the finger cot to maximize comfort for the user. The seam is formed with minimal width, and not being sewn has a highly consistent seam margin. The first and second pieces of material are then trimmed close to the seam to complete the manufacture of the finger cot. When formed in this manner, the seam is located adjacent the backhand side of the finger and adjacent the end of the fingernail, such that seam is not located on the palm face of the finger or the finger tip, where it could interfere with the sensitivity to touch of the users finger. So long as a material or a composite material is chosen which can be welded to itself, a cot can be formed in accordance with this invention from a multitude of materials which may be selected to maximum tactility, or maximum puncture resistance, or some compromise between maximum tactility and maximum puncture resistance.

DETAIL DESCRIPTION OF THE PREFERRED EMBODIMENTS

THE FINGER COT

Figure 1A:
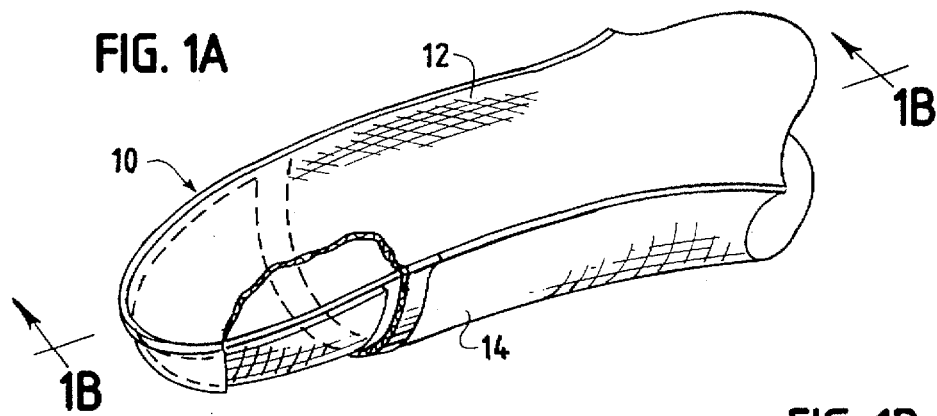
FIG. 1A is a perspective view, with a section adjacent the tip removed, of a finger cot manufactured in accordance with a first embodiment of this invention.
Figure 1B:
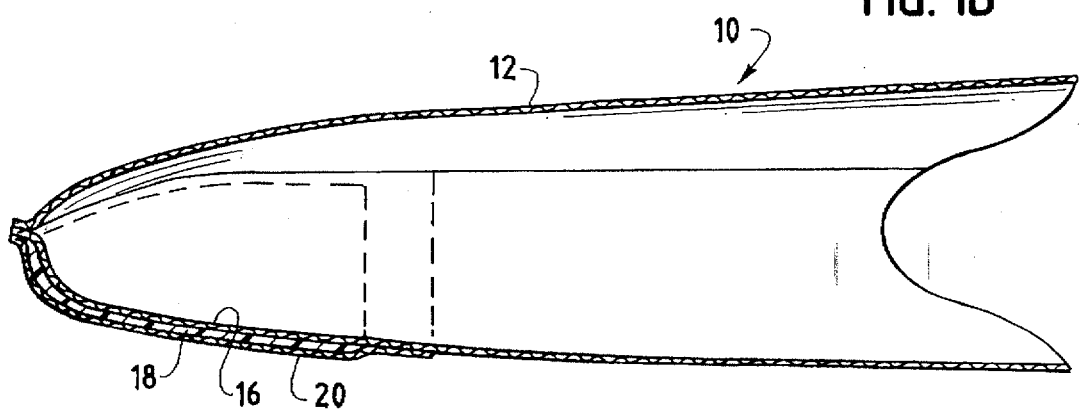
FIG. 1B is a cross section of FIG. 1A.

Referring to FIGS. 1A and 1B, a finger cot constructed in accordance with a first embodiment of this invention will be described. The finger cot 10 is assembled from a top or back portion 12 and a palm face and sides portion 14. A preferred material for the back portion 12 is a base fabric made of 80% Polyester and 20% Spandex to one side of which is laminated to a 0.8 Nil thick Polyurethane film. The palm face and sides portion 14 is formed as a composite construction of an inner layer 16 preferably formed of the same material as the back portion 12, an intermediate layer 18 formed of a more puncture resistant material, and an outer layer 20 preferably formed of the same material as the back portion 12. While the back portion 12 and the inner layer 16 of the palm face and sides portion 14 are made long enough to substantially cover the entire finger, the intermediate layer 18 is intended to cover only the distal phalange portion of the finger, that is from the finger tip to the adjacent joint. The outer layer 20 is made somewhat longer than the intermediate layer 18, so as to cover the intermediate layer and an adjacent portion of the inner layer 16.

The intermediate layer 18 provides an extra measure of protection on the palm side of the cot. This additional layer could be any number of fabrics, composites, plastics, rubbers, etc. The primary consideration in selection of the material for the intermediate layer is that it must be capable of being molded. Thus, it must have flexibility in its normal state or after being heated. One material which has been used for the intermediate layer is Styrene. In its normal state Styrene is quite stiff and must be "softened" by heat to be molded into the desired shape. Another material used for the intermediate layer is flexible clear Vinyl. Cot have been fabricated with both Styrene and Vinyl, with both materials having thicknesses in the range from 0.020" to 0.030". The particular type of intermediate or reinforcement layer used is dependent upon amount of puncture resistance desired taking into consideration the sensitivity/tactility needed.

As will be hereinafter described, in conjunction with a description of the preferred method of making a finger cot in accordance with this invention, the palm face and sides portion 14 is shaped to cover the palm side, tip and sides of the finger. The back portion 12 and palm face and side portion 14 are jointed to each other by a seam formed by an ultra sonic welder. The Polyurethane film acts as an adhesive to laminate the various layers of the finger cot to each other.

While the cot is primarily intended for use over a latex glove, when it is used as a stand alone protective measure, the Polyurethane film provide a measure of protection from blood borne pathogens.

Figure 2A:
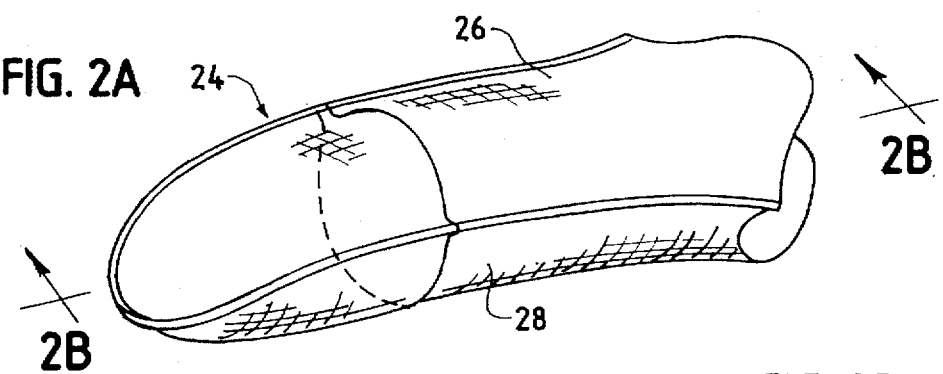
FIG. 2A is a perspective view, of a finger cot manufactured in accordance with a second embodiment of this invention.
Figure 2B:
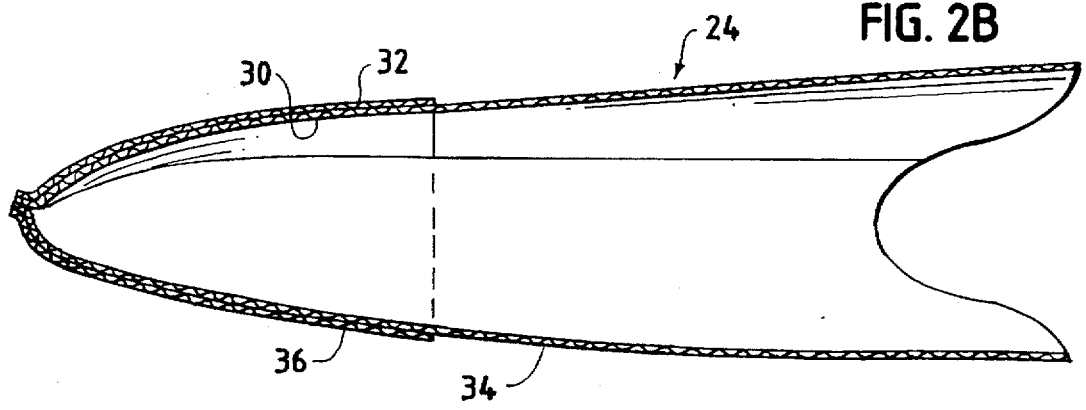
FIG. 2B is a cross section of FIG. 2A.

Referring to FIGS. 2A and 2B, a finger cot constructed in accordance with a second embodiment of this invention will be described. In a non-reinforced finger cot in accordance with the second embodiment, a single layer of the above material is utilized for the entire body of the cot and an extra layer of same material is laminated to the end or tip of the finger on both palm and back side. This double layering provides additional protection to those areas of the finger which will likely incur a higher frequency of puncture. The finger cot 24 is assembled from a top or back portion 26 and a palm face and sides portion 28. The back portion 26 is made from the same material as in the first embodiment. However, it is made with two layers of the material, an inner layer 30 and an outer layer 32 which covers only the distal phalange portion of the finger, that is from the finger tip to the adjacent joint. The palm face and sides portion 28, is made similar to the back portion 26. That is, with two layers of the same material as in the first embodiment, an inner layer 34 and an outer layer 36 which covers only the distal phalange portion of the finger.

While a base fabric made of 80% Polyester and 20% Spandex to one side of which is laminated to a 0.8 Mil thick Polyurethane film is presently the preferred material as previously set forth, other materials could be used depending upon the degree of resistance to cutting and puncture which is desired, balanced against the degree of sensitivity or tactility needed to perform a specific task using the cot.

However, there are two mandatory qualities required in any type of material or composite material used: 1. A significant amount of stretch, and 2. The ability to be heat sealed to itself and if laminated to another material.

While fabrics such as those made of 100% Cotton or Wool most likely would not be utilized in the finger cot, many man-made materials such as fabrics made from Polyester, Nylon, Polypropylene, Acrylic, etc. and blends thereof could be used.

THE MANUFACTURING PROCESS

The manufacturing process consists of at least four basic operations:

A. Cutting of Blanks

Figure 3:
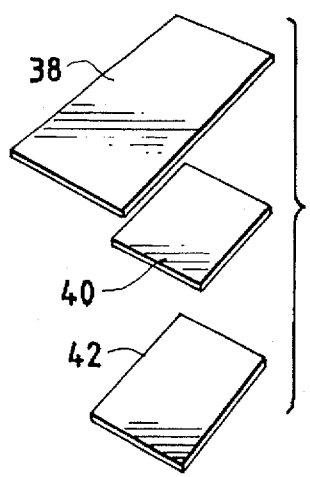
FIG. 3 is a perspective view three blanks used to form the palm side of the finger cot of FIG. 1.

A reinforced cot in accordance with the first embodiment of the invention requires a total of three blanks for the palm side as shown in FIG. 3. A large or inner blank 38 and a smaller or outer blank 42 are formed of a piece of the base fabric made of 80% Polyester and 20% Spandex on which is placed a piece of 0.8 Mil thick Polyurethane film. The intermediate blank 40 is a piece of styrene, clear vinyl or other material as previously described. The inner blank 38 forms the inner layer 16, the intermediate blank 40 the intermediate layer 18 and the outer blank 42 the outer layer 20. For the back portion of a finger cot in accordance with the first embodiment, only a single blank like 38 is required. Both the back portion 26 and palm face and sides portion 28 of a non-reinforced finger cot in accordance with the second embodiment require two blanks, such as 38 and 42. Of course there could also be variations on either type of cot by adding extra layers or using different materials for each layer.

B. Lamination of Cut Blanks

Figure 4:
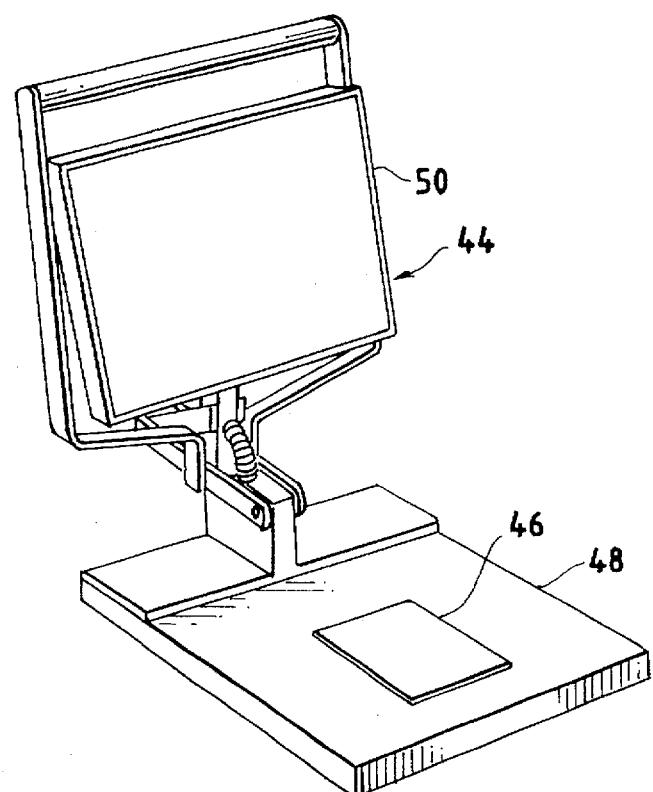
FIG. 4 shows the three blanks of FIG. 3 position in an open heat and pressure press.
Figure 5:
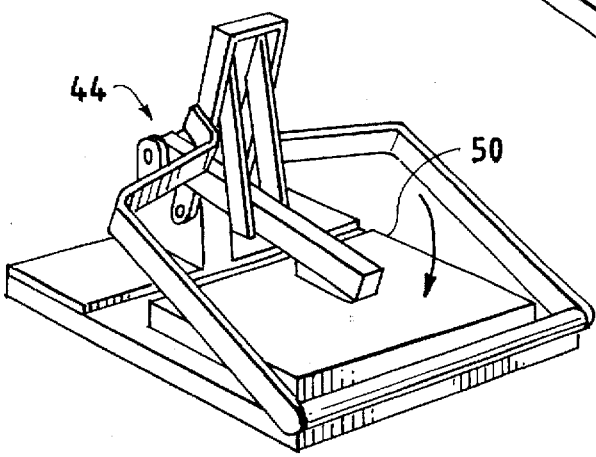
FIG. 5 shows the heat and pressure press of FIG. 4 closed so as to apply heat and pressure to the three blank shown in FIG. 3.

In the non-reinforced cot one small size cut blank 42 laminated to one large size cut blank 38 with the polyurethane film side of each blank arranged face to face. This operation is performed through the use of heat and pressure. As shown in FIG. 4, a press 44 such as is normally used to apply heat transfers to articles of clothing may be used. The stacked blanks 46 are placed on the base 48 of the press, and the cover 50 is then lower to rest on the stacked blanks 46 to apply heat and pressure thereto as shown in FIG. 5.

In a reinforced cot the intermediate layer of material (plastic, vinyl, etc.) is sandwiched between the inner and outer layers and all three layers are laminated in a single operation.

C. Molding, Cutting and Welding of laminated blanks

Figure 6:
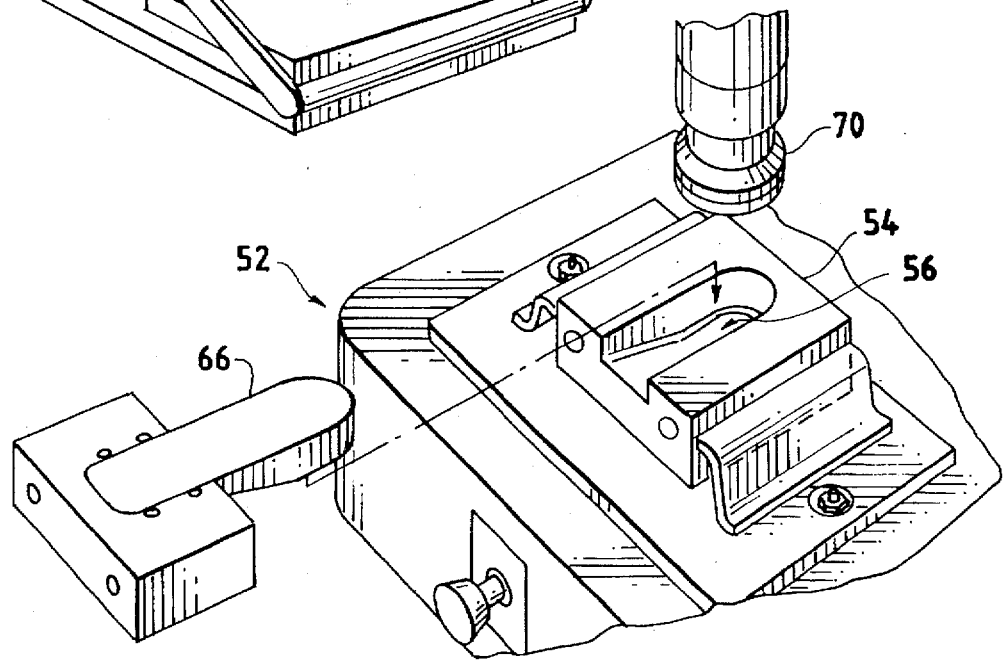
FIG. 6 shows an anvil with a cavity and the male insert received in the cavity of an ultrasonic welding machine use to manufacture a finger cot in accordance with this invention.
Figure 7:
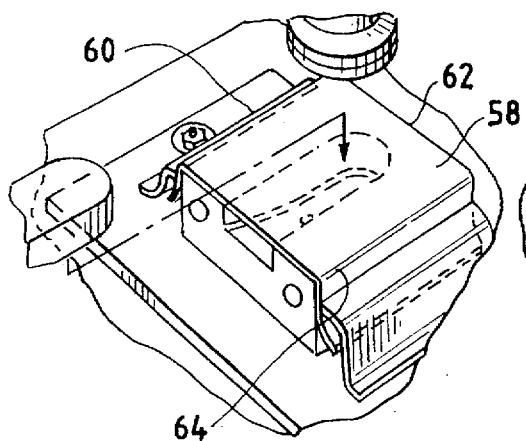
FIG. 7 shows the composite material formed by the heat and pressure press of FIGS. 4 and 5 clamped on three side of the anvil shown in FIG. 6.

The molding, cutting and welding of laminated blanks is performed in an ultra sonic welding machine and press 52, such as is shown in FIGS. 6–10. Referring to FIG. 6, the ultra sonic welding machine and press 52 is provided with an anvil 54 having a cavity 56 formed therein having the shape of a finger. A laminated blank 58 forming the palm face, sides and tip of a finger cot is placed over the anvil 54 and draped into the cavity 56 of the anvil. Three sides 60, 62, and 64 of the blank 58 are then clamped to the anvil to prevent movement of the blank material which is essential in order to obtain a specific size of finger cot. By using anvils having two different sized cavities 56, it is possible to produce four different sizes of finger cots, small and medium size cots with the smaller cavity, and large and extra large size cots with the larger cavity. The specific size desired is obtained by regulating the amount of material draped into the cavity 56 of the anvil 54 prior the clamping the three sides 60, 62 and 64 of the blank 58.

Figure 8:
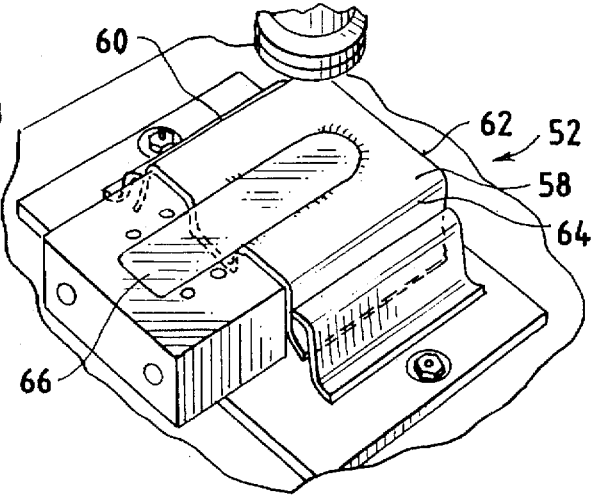
FIG. 8 shows the male insert placed on top of the composite material and in the cavity of the anvil as shown in FIG. 6.

The next step is to place an insert 66 into the cavity 56 of the anvil 54 over the laminated blank 58 as shown in FIG. 8. The insert 66 is machined to the same shape as the cavity 56, except somewhat smaller to allow a gap for material of laminated blank 58 to fit between the walls of the cavity and the insert.

Figure 9:
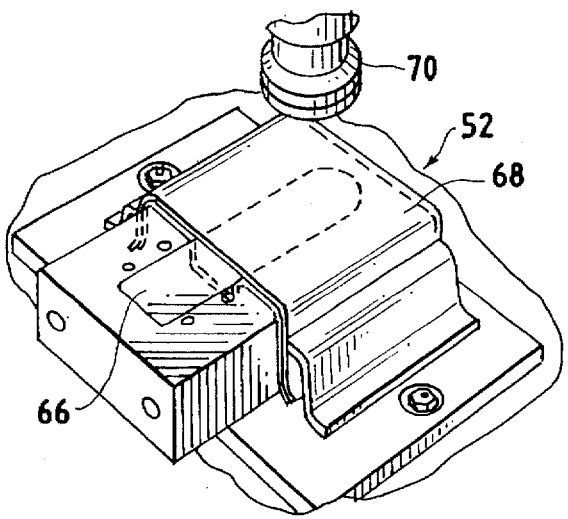
FIG. 9 shows the material forming the back side of the finger cot place over the male insert and extending over the exposed portions of the composite material forming the palm side of the finger cot as shown in FIG. 8.

In the following step a second laminated blank 68 to form the back portion of the finger cot is laid on top of the anvil 54 over the insert 66 and the exposed portions of the blank 58 as shown in FIG. 9. The second laminated blank 68 need not be clamped in any way.

Figure 10:
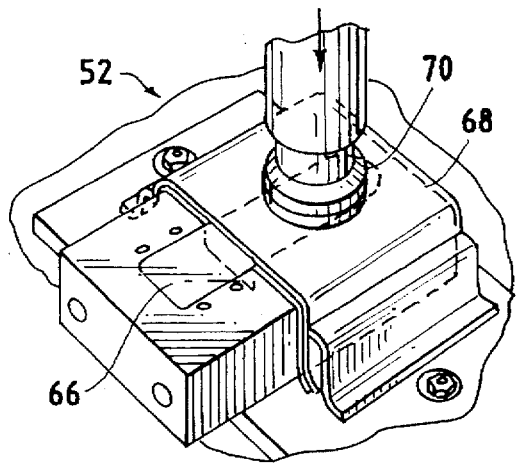
FIG. 10 shows the sonic welding head engaging the anvil and the composite material resting there-over to weld the seams along the edges of the cavity and to cut the welded material along the outside edges of the welded seam.
Figure 11:
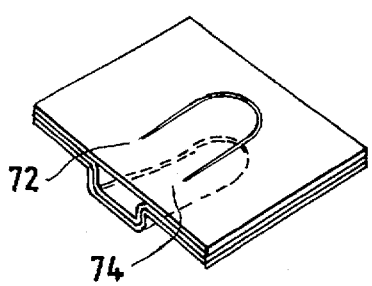
FIG. 11 shows the welded finger cot with the excess material surrounding the weld still attached adjacent the open end of the cot.

In the next step the operating head of the ultra sonic welding machine and press is activated and a horn (vibrating head) 70 descends and meets a cutting blade which surrounds the cavity 56 and is the uppermost portion of the anvil as shown in FIG. 10. The operating head or horn forces the insert 66 into the cavity 56 and molds or form the palm face, sides and tip of a finger cot. When the horn 70 touches the cutting blade, the blanks 58 and 68 are welded to each other so as to form a continuous narrow seam, and cut along the outer edge of the seam so as to form a finished finger cot as shown in FIG. 11, except for a trimming operation to remove scrap material which remains attached at 72 and 74. This operation provides a cot having a desired three dimensional form, and provides an absolute minimum amount of "seam" width, which is located on the outside of the finger cot.

D. Trimming of finger cot

Figure 12:
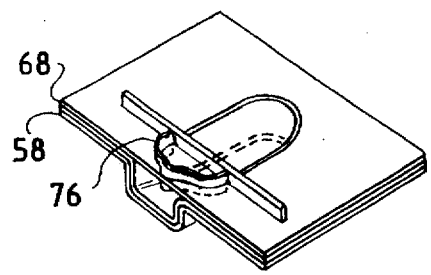
FIG. 12 shows a trim die positioned over the cot as shown in FIG. 11 in the position to cut and free the excess material from the cot.

The final operation is to trim off the remaining scrap on a machine using a standard cutting die 76 as shown in FIG. 12. The cutting die 76 severs the scrap from the finger cot and trims the back and palm portions of the cot at its inner end.

While several embodiments of the invention have been shown, it should be apparent to those skilled in the art that what has been described are considered at the present to be the preferred embodiments of the finger cot and the method of making the same of this invention. In accordance with the Patent Statutes, changes may be made in the finger cot and the method of making the same of this invention without actually departing from the true spirit and scope of this invention. The following claims are intended to cover all such changes and modifications which fall in the true spirit and scope of this invention.

What is claimed:

1. A finger cot comprised of at least two blanks of material having peripheral edges, a first one of said blanks forming the palm face, tip and side portions of the finger cot and a second one of said blanks forming the back portion of the finger cot, said peripheral edges of said blanks being secured to each other to form a seam therebetween, said seam at the tip of the finger cot being adjacent the finger nail, and said seam extending the length of the finger being substantially centered between the back side and side of the finger such said seam is not located on the finger surfaces which are normally used to touch or grasp an object and a third blank of material overlies said tip and adjacent front portion of said first blank of material so as to provide reinforcement of the portion of said finger cot most likely to be subjected to puncture or cutting, the third blank of material limited to the area extending from the finger tip to the first joint of the finger so as to avoid reducing the flexibility and tactile nature of the finger cot, the third blank of material thermally laminated to the first blank of material.

2. The finger cot of claim 1, wherein said seam is formed by ultra sonic welding.

3. The finger cot of claim 1, wherein said blanks of material are formed from with a base fabric of 80% Polyester and 20% Spandex, one side of said base material being laminated to a polyurethane film.

4. The finger cot of claim 1, wherein a fourth blank formed from a second material which will provide additional protection from cutting and puncture wounds is placed between said first and third blanks of material.

5. The finger cot of claim 4, wherein said fourth blank is formed from a material selected from the group consisting of styrene and vinyl.

* * * * *